United States Patent [19]

Takahashi et al.

[11] 4,436,388
[45] Mar. 13, 1984

[54] EYE-FUNDUS CAMERA PROVIDED WITH AUTOMATIC FOCUSING FUNCTION

[75] Inventors: Junichi Takahashi, Kawasaki; Toshio Sakane, Yokohama; Yuji Itoh, Chigasaki, all of Japan

[73] Assignee: Canon Kabushiki Kaisha, Tokyo, Japan

[21] Appl. No.: 252,878

[22] Filed: Apr. 10, 1981

[30] Foreign Application Priority Data

Apr. 25, 1980 [JP] Japan .................. 55-55068

[51] Int. Cl.³ .............................................. A61B 3/14
[52] U.S. Cl. ..................................... 351/206; 354/62; 351/208
[58] Field of Search ................ 351/6, 7, 16, 206, 207, 351/208; 354/62

[56] References Cited
U.S. PATENT DOCUMENTS 3,614,214 10/1971 Cornsweet .
3,925,793 12/1975 Matsumura .
4,264,153 4/1981 Ito ...................................... 354/62

Primary Examiner—John K. Corbin
Assistant Examiner—Rodney B. Bovernick
Attorney, Agent, or Firm—Fitzpatrick, Cella, Harper & Scinto

[57] ABSTRACT

An eye-fundus camera provides change-over and selection between automatic focusing and manual focusing. The eye-fundus camera includes a projector, a photo-sensor array, a focus controller and an illuminator. The projector projects a first focus mark and a second focus mark on the fundus of an eye to be examined. The photo-sensor array detects the first focus mark reflected from the fundus and the output from the sensor array is introduced into the controller to adjust the focus of the camera. The illuminator illuminates the fundus uniformly with light within a first wavelength range. The first focus mark is with light within the first wavelength range and within a second wavelength range other than the first one whereas the second focus mark is formed only of light within the first wavelength range. The eye-fundus camera further comprises a wavelength selecting mirror which cuts off light of the first wavelength range among rays of light incident upon the photo-sensor array.

12 Claims, 12 Drawing Figures

EYE-FUNDUS CAMERA PROVIDED WITH AUTOMATIC FOCUSING FUNCTION

BACKGROUND OF THE INVENTION

1. Field of the Invention

The present invention relates to an eye examining instrument, and more particularly to a system for focusing the instrument on the fundus of an eye to be examined. The present invention is also directed to improvements in the eye-examining apparatus alreaady proposed by our prior applications, U.S. application Ser. No. 109,275 (abandoned in favor of continuation U.S. application Ser. No. 346,870, filed Feb. 2, 1982), and Ser. No. 180,103.

2. Description of the Prior Arts

In a conventional eye-fundus camera, focusing on the eye has been achieved by adapting the sight of the eye to cross-hairs in a finder and by adjusting the photographing lens in such a manner that the eye-fundus can be clearly viewed in this state. However this focusing method inevitably involves fluctuation during an examination and is difficult to conduct rapidly.

U.S. Pat. No. 3,925,793 (German Pat. No. 2,415,319) and U.S. patent application Ser. No. 945,845 now U.S. Pat. No. 4,283,124 relate to a focusing method by projecting plural marks on the eye-fundus and aligning the marks under observation. Although rapid focusing has been rendered possible by these methods, there still remains a strong demand for automatic focusing of the camera, as the setting of an eye-fundus camera simultaneously requires alignment of the eye axis with the optical axis of the objective lens, distance adjustment between the cornea and the objective lens and focus adjustment. The operator has to constantly pay attention to these three factors as the above-mentioned alignment and distance are easily affected by small movements of the subject to be examined while the focusing is affected by a change in the sight of the eye to be examined. For this reason automatic focusing, if realized, will significantly alleviate the load on the operator and contribute to the probability of obtaining photographs of improved image quantity.

As a pioneer invention for automatic focusing of the eye-fundus camera to the eye ground there is U.S. Pat. No. 3,614,214, in which a dichroic mirror reflecting infrared light but transmitting visible light is provided in front of an ordinary eye-fundus camera in an oblique position to deflect a detecting beam from an automatic optometer toward the eye to be examined and to again deflect reflected beam from the eye to the optometer, whereby the focusing lens of the eye-fundus camera being adjusted by the output of the optometer.

As readily seen from the above, the known eye-fundus cameras need refocusing even after the camera has once been focused on the fundus if the subject moves even very slightly or any change occurs in the sight of the subject eye. In this case there exists some time lag as a matter of course. Therefore it is desirable to display the state of focusing with means such as a focus mark. If such a focus mark display is realized, it will enable the operator or examiner easily to release the shutter because he can confirm that the apparatus is in-focus by viewing the focus mark. Furthermore, the operator can release the shutter at the proper time which in turn serves to improve the image quality. In addition, such focus mark display will make it possible to carry out manual focusing rapidly.

However, the use of a focus mark in an eye-fundus camera involves problems. The focus detecting light reflected upon the fundus and guided to the view-finder enters a photodetector and constitutes noise by which the accuracy of detection is substantially reduced.

SUMMARY OF THE INVENTION

Accordingly it is an object of the invention to make it possible to observe a focus mark projected on the fundus for automatic focus detection.

It is another object of the invention to improve the accuracy of detection by cutting off any undesirable light entering the automatic focus detector.

It is a further object of the invention to provide an eye-fundus camera in which the change-over and selection in a focusing operation mode can be made between automatic focusing and manual focusing.

Other and further objects, features and advantages of the invention will appear more fully from the following description taken in connection with the accompanying drawings.

DESCRIPTION OF THE PREFERRED EMBODIMENTS

Figure 1:
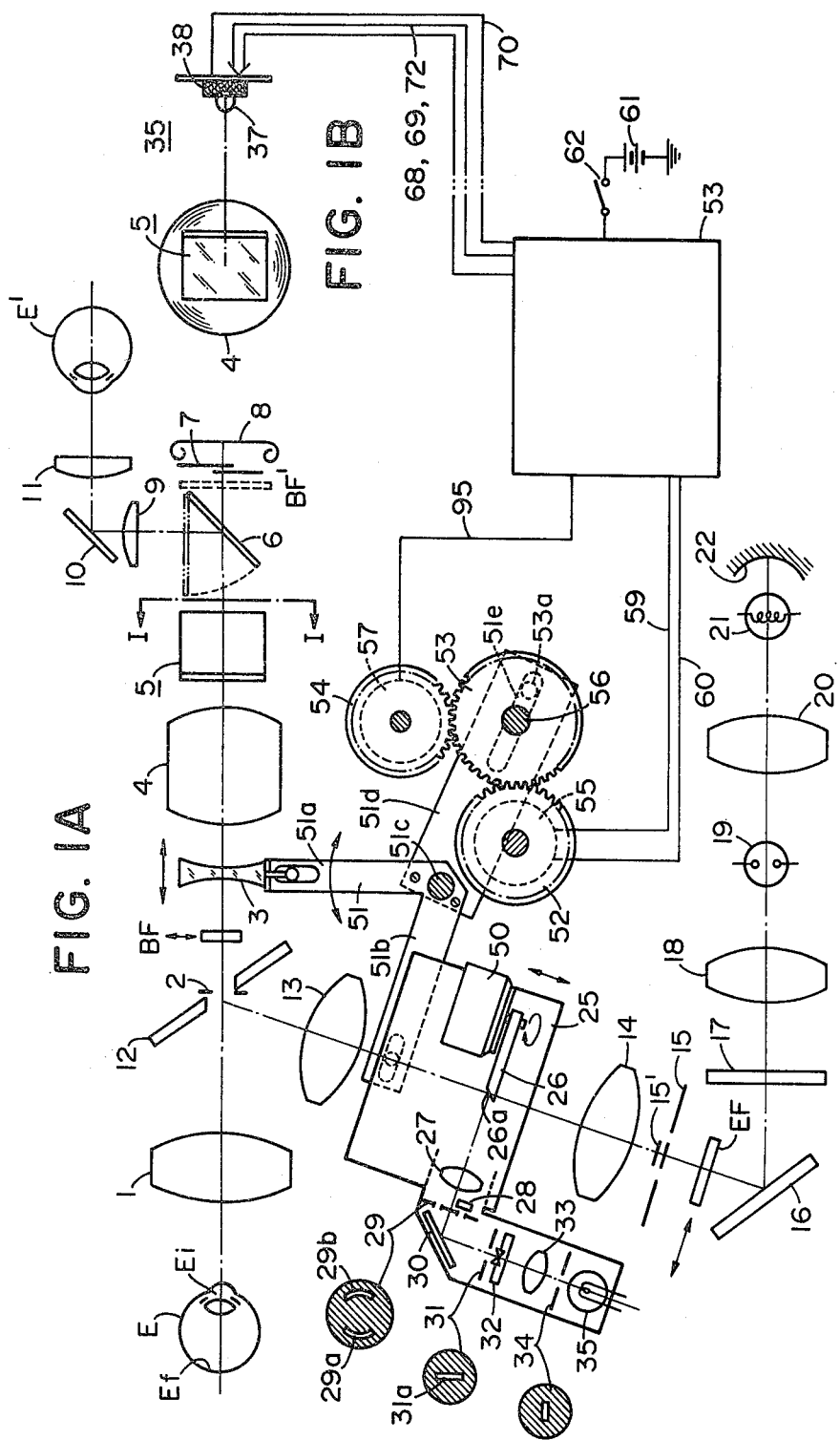
FIG. 1A is an optical cross-sectional view of an embodiment of the present invention.
FIG. 1B is a cross-section taken along the line I—I in FIG. 1A.

In FIGS. 1A and 1B showing an embodiment of the invention, an eye to be examined is designated by E, its fundus by Ef and its pupil by Ei. Reference numeral 1 designates an objective lens, 2 a diaphragm, 3 a focusing lens movable along the optical axis and 4 indicates an imaging lens. Designated by 5 is a dichroic mirror having a multi-layer interference film vapour-deposited thereon. The dichoric mirror 5 is disposed at an inclination of 45° relative to the optical axis. The optical characteristics of the dichroic mirror 5 are shown in FIG. 2, wherein it can be seen that the mirror 5 transmits the visible range of light but reflects the infrared range of light (including infrared and near infrared rays) corresponding to the spectral sensitivity of a focus detector as hereinafter described.

6 is a quick return mirror. For observation, the mirror 6 is disposed obliquely in the optical path as indicated by the solid line. For taking a picture, it is retracted to a position out of the optical path as suggested by the phantom line. 7 is a shutter which is released by operating a releasing means (not shown). The releasing operation can be carried out independently of the operation of automatic or manual focus control as hereinafter described. 8 is a photographing film.

The above mentioned objective lens 1, diaphragm 2, focusing lens 3, imaging lens 4, shutter 7 and film 8 constitute together a picture taking system. An image of the eye fundus Ef is once formed by the objective lens 1 and an intermediate image is refocused on the film 8 by the focusing lens 3 and imaging lens 4.

Designated by 9 is a field lens disposed on an observation plane equivalent to the film plane relative to the mirror 6. 10 is an optical path deflecting mirror and 11 is an eyepiece. The mirror 6, field lens 9, a mirror 10 and an eyepiece 11 constitute together a finder system. E' indicates an eye of the examiner.

Figure 3:
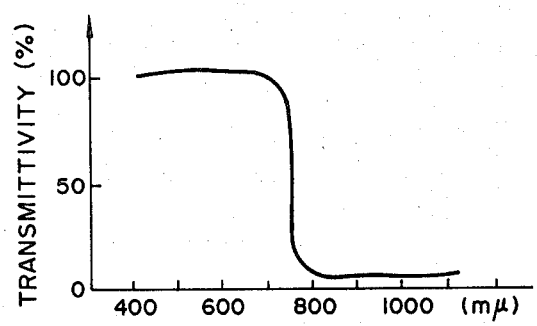

Designated by 12 is a bored mirror having an opening lying on the optical axis and a mirror surface disposed obliquely to the optical axis. 13 and 14 are relay lenses. 15 is a screen plate having a ring slot, 15' is a small screen plate and 16 is an optical path deflecting mirror. 17 is an infrared cut filter whose optical characteristic is shown in FIG. 3. As seen in FIG. 3, the filter 17 transmits the visible range of light and cuts off the infrared range of light. 18 and 20 are condenser lenses, 19 is a light source for observation such as a xenon lamp, 21 is a light source for picture taking such as a halogen lamp and 22 is a concave mirror for condensing rays of light. These members 12 through 22 and the objective lens 1 constitute an illumination system.

The beams of light emitted from the light sources 19 and 20 are concentrated on the screen plate 15 under the action of the condenser lenses 18 and 20. The beam of light emerging from the ring opening of the screen plate 15 is then focused in the vicinity of the pupil Ei through the relay lenses 13 and 14, and the objective lens 1 to illuminate the fundus Ef. The function of the small screen plate 15' is to cut off a portion of the illumination light so as to shadow the surface of the crystalline humour on the side of the fundus thereby preventing the light from being reflected or scattered by the crystalline humour in a manner known per se.

The apparatus shown in FIG. 1 includes a focus mark projection system as described in detail hereinafter.

Figure 4:
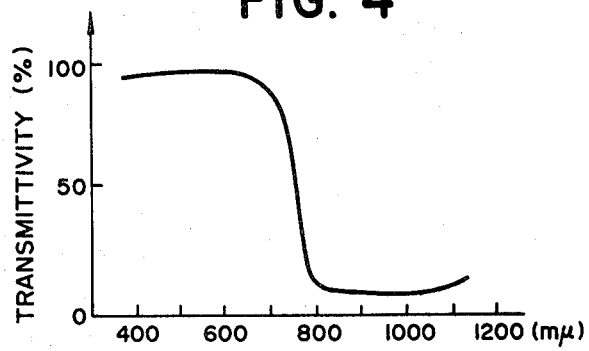

The focus mark projection system comprises a supporting member 25 mounted movably in the direction indicated by a double arrow. A mirror rod 26 on the supporting member is, at its one end, fixed to the axis of rotation of a rotary solenoid 50. At the other end, the mirror rod 26 has a mirror surface 26a which intersects the optical axis of the illumination system at an angle of 45°. Actuation of the solenoid 50 is coordinated with the shutter releasing operation and the shaft to which the mirror rod 26 is fixed starts rotating to retract the mirror rod toward the outside of the optical path during the time when a picture of the fundus is being taken. 27 is a projection lens and 28 is a filter which transmits the visible range of light but cuts off the infrared range of light. 29 is a double slitted plate having two arcuate slits 29a and 29b formed therein. One of the two slits is covered with the filter 28 whose characteristic curve is shown in FIG. 4. The beam of light emerging from the slit is used for observation. The other slit is not covered with any filter and the beam of light emerging from this slit is useful for both focus detection and observation. If there is available in the structure sufficient space to keep focus marks described hereinafter apart from each other adequately, then the filter 28 may be omitted.

30 is an optical path deflecting mirror and 31 is a slit plate. The slit plate 31 has a linear slit 31a formed therein to provide a focus mark. 32 is a split prism comprising a double prism at the middle thereof. The split prism 32 functions as two optical wedges oppositely tapered and bounded by a boundary extending normal to the plane of the drawing. Under the function of the optical wedges, the split prism 32 splits the incident beam into two beams which are refracted in the directions opposite to each other. The order in arrangement of the slit plate 31 and the split prism 32 may be reversed. Also, the slit plate and the split prism may be disposed very closely to each other or conjugated with each other. 33 is a condenser lens, 34 is a visual field limiting mask and 35 is a light source. The light source 35 emits the visible and infrared ranges of light to illuminate the slit plate 31.

The above mentioned double slitted plate 29 is disposed approximately conjugated with the pupil of the eye relative to the projection lens 27, relay lens 13, the mirror surface of the bored mirror 12 and also to the objective lens 1. The two slits formed in the plate 29 are disposed horizontally. The focus mark projection system is moved in the direction of the optical axis in synchronism with the motion of the focusing lens 3 so that the mirror surface of the mirror rod 26 can be kept always at a position equivalent to the position of the film 8. Therefore, the film 8 and the fundus Ef are also conjugate to each other. Furthermore, the slit plate 31 and the mirror surface 26a are conjugate to each other relative to the projection lens 27.

Figure 2:
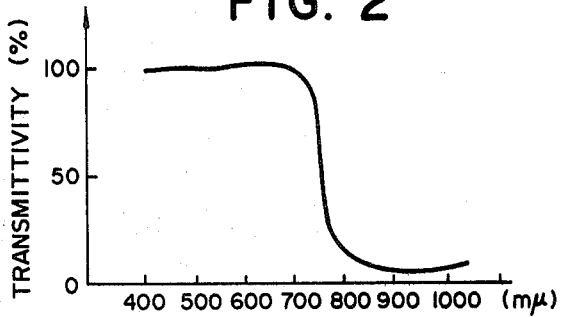
FIGS. 2 to 4 show optical characteristic curves.

FIG. 1B shows the arrangement of a focus mark receiving system 35 which is composed of the above mentioned wavelength-splitter (dichroic mirror 5), a linear photo-sensor array 38 and a cylindrical lens 37. In the photo-sensor array, a plural number of sensor elements are arrayed in the direction normal to the plane of FIG. 1 drawing. The photo receiving surface of the sensor array 38 is equivalent to the film plane 8 or observation plane relative to the mirror surface of the dichroic mirror 5. Therefore, the photo receiving surface of the sensor array 38 and the eye-fundus Ef are always conjugate so long as the film 8 and the fundus Ef are conjugate to each other. To increase the concentration of light and also to improve the ratio of signal to noise (S/N), the cylindrical lens 37 is disposed in such manner that it can exhibit a refractive power within a plane extending in parallel with the plane of the drawing and also its focal plane can be coincident with the photo receiving surface of the linear photo-sensor array 38.

The focusing lens 3 and the focus mark projection system (housed in the supporting member 25) are connected with each other through a connection arm 51. The connection arm is swingable about a pivot 51c and has two elongate slots at both of its ends. Engaged in one elongate slot at one end 51a of the arm 51 is a pin connected with the focusing lens 3. Engaged in the other slot at the other end 51b is a pin secured to the supporting member 25. Owing to these pin-slot joints, it is possible to adjust the positional relation between the focusing lens 3 and the supporting member 25 by the pivotable motion of the connection arm 51. Designated by 56 is a driving shaft which can be connected to a manual adjustment dial or the like through a clutch not shown. When manual focusing is desired, the clutch is actuated and then the manual adjustment dial is turned. Mounted on the driving shaft 56 for rotation therewith is a gear 53 having a cam pin 53a standing from the backside surface thereof. The cam pin 53a is engaged in an elongate slot 51e provided in one length 51d of the connection arm member 51. As the gear 53 is driven into rotation, the arm 51d rotates about the pivot 51c so as to move the focusing lens 3 and the focus mark projection system.

The gear 53 is in mesh with a gear 52 which is driven into clockwise or counter-clockwise rotation by a serve-motor 55. The gear 53 is in mesh with another gear 54 with which a potentiometer 57 is connected.

Therefore, the potentiometer can detect the amount of rotation of the driving motor 55 and the amount of displacement of the focusing lens 3.

Designated by 58 is a signal processor of which a detailed description will be made hereinafter. The signal processor 58 receives an output signal on line 70 from the focus mark projection system 35 and issues driving signals on lines 59 and 60 to rotate the motor 55 in a determined amount of rotation corresponding to the signal on line 70. The amount of rotation executed by the motor is fed back to the processor from the potentiometer 57 through a connection line 95. The signal processor is powered from a power source 61 through a switch 62. It is recommended that the clutch mentioned above be interlocked with the switch 62 in such manner that the clutch is connected with the driving shaft 56 when the switch is opened and is disconnected when the switch is closed.

In the above arrangement of the apparatus, a beam of light emitted from the light source 35 enters the split prism 32 which, as previously mentioned, diffracts and splits the beam. After passing through the slit plate 31, the beam is divided into the two beams in the middle of the slit 31a. One of the two beams is refracted toward one of the two slit openings 29a and 29b and the other beam is refracted toward the other slit opening. Under the action of the projection lens 27, the beams passed through the slits 29a and 29b form an image of the slit 31a on the mirror surface of the mirror rod 26. The light of image is reflected by the mirror surface and is again divided into two beams which enter the eye E through the relay lens 13, bored mirror 12 and objective lens 1. As two oblique beams inclined oppositely to each other, the beams each form one image of the corresponding half of the slit on the fundus or before or after the fundus. Namely, an image of one half of the slit and an image of the other half are focused on or before or after the eye-fundus as focus marks. At this time, if the two oblique beams are focused just on the fundus, then the focus marks will be in alignment with each other. On the contrary, if the oblique beams are focused at positions in front of or behind the fundus, then the focus marks appearing on the fundus are not in alignment with each other and therefore the focus marks become somewhat blurred. This is because the two oblique beams are cut off by the fundus before or after the beams intersect each other. Since the focus marks come close to each other or go away from each other by changing the focused position, the focus marks can be brought into alignment by a focus adjusting operation. When the focus marks get in alignment with each other, it means that a coincidence of the focused position and the fundus is attained.

The light sources 19 and 21 are approximately conjugate relative to the condenser lens 20. Through another condenser lens 18, the light sources illuminate the screen 15 provided with a ring slit and they form a ring-shaped secondary light source at the screen 15. An image of the secondary light source is formed on the bored mirror 12 which reflects the image toward the objective lens 1. The objective lens 1 forms again an image of the secondary light source on the pupil Ei of the eye to be examined. The image of the secondary light source illuminates the eye fundus Ef uniformly throughout a wide range thereof. For observation, the light source 21 is turned on whereas the light source 19 is turned on for taking a picture of the fundus.

The split focus mark emerging from the focus mark projection system 25 is focused on the fundus Ef through the relay lens 13, bored mirror 2 and objective lens 1. The illumination light reflected upon the fundus Ef passes through the refracting system of the examined eye E and the objective lens 1 and then forms an intermediate image on the focal plane of the latter. After passing through the center opening of the bored mirror and the diaphragm 2, the reflected light is focused on the film 8 through the focusing lens 3 and imaging lens 4. For observation, the quick return mirror 6 is in its working position in front of the film plane. Therefore, the examiner E' can observe the image of the fundus through the finder system (9 to 11). During the time of this observation, the examiner checks the alignment of the focus marks in the image of the fundus. If the focus marks are out of alignment and appear apart from each other on the fundus, the examiner manually rotates the driving shaft 56 while observing the fundus image through the finder system so as to bring the focus marks in alignment. In this manner, manual adjustment of the focal point can be conducted very easily.

Figure 5:
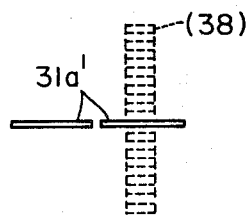
FIG. 5 is a plan view of a focus mark.

The focus mark projected on and reflected by the fundus enters the dichroic mirror 5 which reflects only the infrared rays of the incident light toward the cylindrical lens 37, that is, in the direction normal to the plane of the drawing of FIG. 1. Through the cylindrical lens, the reflected light of the focus mark is focused on the linear photo-sensor array 38. Since, as previously noted, the filter 28 in the focus mark projection system inhibits the transmission of infrared light through one of two equal slit parts 29a and 29b, only one half of the reflected focus mark from the fundus is directed to the sensor array 38 by the dichroic mirror 5. In the case of the focus mark projection system in this embodiment, the focus mark 31a', when it is in focus, will appear on the fundus in a form as shown in FIG. 5. The same form of focus mark as shown in FIG. 5 appears also on the observation plane and the picture taking plane because the filter 28 and also the dichroic mirror 5 transmit the visible range of light. The half of the focus mark reflected by the dichroic mirror 5 and focused on the linear photo-sensor array 38 in the shown form lies on the array with length of the focus mark extending in the direction normal to the scanning direction of the array as seen also in FIG. 5. Since the position where the focus mark is formed is variable depending upon the refractive power of the examined eye, it is required to detect at first the initial position of the focus mark and then adjust the focus mark projection system so as to bring the focus mark to the reference position on the sensor array (the reference position is a position at which the focus mark appears when the fundus and the film become conjugated with each other).

Also, since the filter 17 in the illumination system has the characteristic shown in FIG. 3, the fundus is never illuminated by infrared light at the time of illumination for observation. Therefore, the image formed on the linear sensor array is only an image of an infrared focus mark which improves the accuracy of detection.

The motor 55 drives the driving shaft 56 into rotation in accordance with the outputs on lines 59 and 60 from the signal processor 58 which is in turn connected with the driving shaft through gears 53 and 52. The driving shaft 56 moves the focus mark projection system 25 and the focusing lens 3 together through the connection arm 51. The driving shaft 56 drives also the gear 54 and the potentiometer 57 together through the gear 53. The potentiometer 57 gives the signal processor a signal determined by the position of the focusing lens 3. Changeover of manual/automatic focusing is conducted by power source 61 and electric switch 62. For automatic focusing, the switch 62 is closed to bring the signal processor 58 into operation. The signal processor 58 is electrically connected to the above mentioned linear photo-sensor array 38 to receive the output signal from the sensor array and to detect the position of the focus mark. Receiving the signal from the sensor array, the processor issues signals to drive the motor 55 in accordance with the detected position of the focus mark. The motor rotates until the focus mark gets in the reference position on the sensor array.

In the above, the automatic focusing operation of a fundus camera has been described particularly in connection with ordinary fundus photographing and fundus observation. As a special fundus photographing method, however, there has been known and often used so-called fluorescent-photography. The manner of focusing operation of the illustrated embodiment for fluorescent-photography will be described in detail hereinafter.

To take a picture of eye-fundus employing the fluorescent-photography, fluorescent sodium is used as a contrast medium. The contrast medium is injected into the vein at the elbow of a person whose eye is to be examined. After lapsing of a sufficient waiting time required for the injected contrast medium to reach the circulatory system in the eye, the fundus of the eye to be examined is illuminated with blue exciting light. The contrast medium in the blood vessel of the eye emits greenish yellow fluorescence, a picture of which is taken using a fundus camera.

Figure 6:
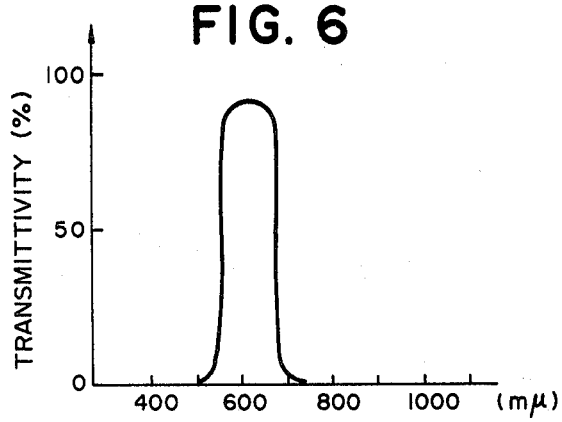
FIGS. 6 to 8 show optical characteristic curves.
Figure 8:
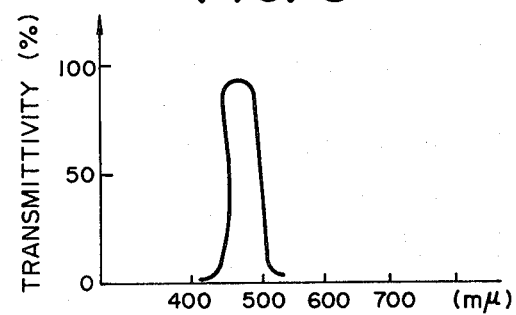

To carry out the above fluorescent-photographing of an eye-fundus, conventionally an excitor filter EF is interposed in the optical path of the illumination system and a barrier filter BF is interposed in the optical path of the picture taking system of the fundus camera. The excitor filter EF exhibits a light transmission characteristic as shown in FIG. 8 and is colored in blue. The filter transmits exclusively such component of white light which falls within the range of wavelength most suitable for exciting fluorescent material. The barrier filter is called also screen filter and is colored in greenish yellow. The filter exhibits a light transmission characteristic as shown in FIG. 6 and transmits exclusively the fluorescent light component of the reflected light from the fundus. For conventional fundus cameras, these filters are necessary for wavelength separation of light when a picture of eye fundus is to be taken employing the fluorescent-photography.

Figure 7:
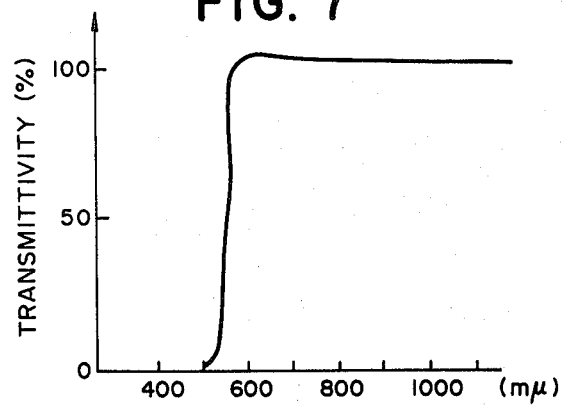

In contrast, according to the invention, there is used as the barrier filter BF such filter which has a characteristic as shown in FIG. 7. The conventional barrier filter (FIG. 6) cuts off rays of light longer than about 700 m$\mu$. In contrast, the barrier filter (FIG. 7) used in the invention transmits also the long wavelength range of light useful for focus detection. Therefore, in the arrangement of the fundus camera according to the invention, the infrared rays of light contained in the half of the focus mark reflected from the fundus can pass through the barrier filter BF and the infrared rays are reflected by the dichroic mirror 5 toward the linear photosensor array 38. Consequently, automatic focusing for fluorescent-photography can be performed in the same manner as described above for ordinary fundus photographing process.

If it is wished to use a barrier filter of conventional characteristic (FIG. 6) in the illustrated embodiment without losing the benefit of automatic focus control, the barrier filter should be interposed between the dichroic mirror 5 and the film 8, for example, at the position of BF'. By doing so, it is made possible to enjoy the benefit of automatic focus adjustment even employing a conventional barrier filter.

The exciter filter EF is a band-pass filter which transmits only a narrow wavelength range of light lying in the neighbourhood of 480 m$\mu$. Therefore, in case that the light conducting mirror 26a of the focus mark projection system is disposed in the illumination light path, the exciter filter EF should be interposed between said mirror 26a and the photographing light source 19.

Figure 9:
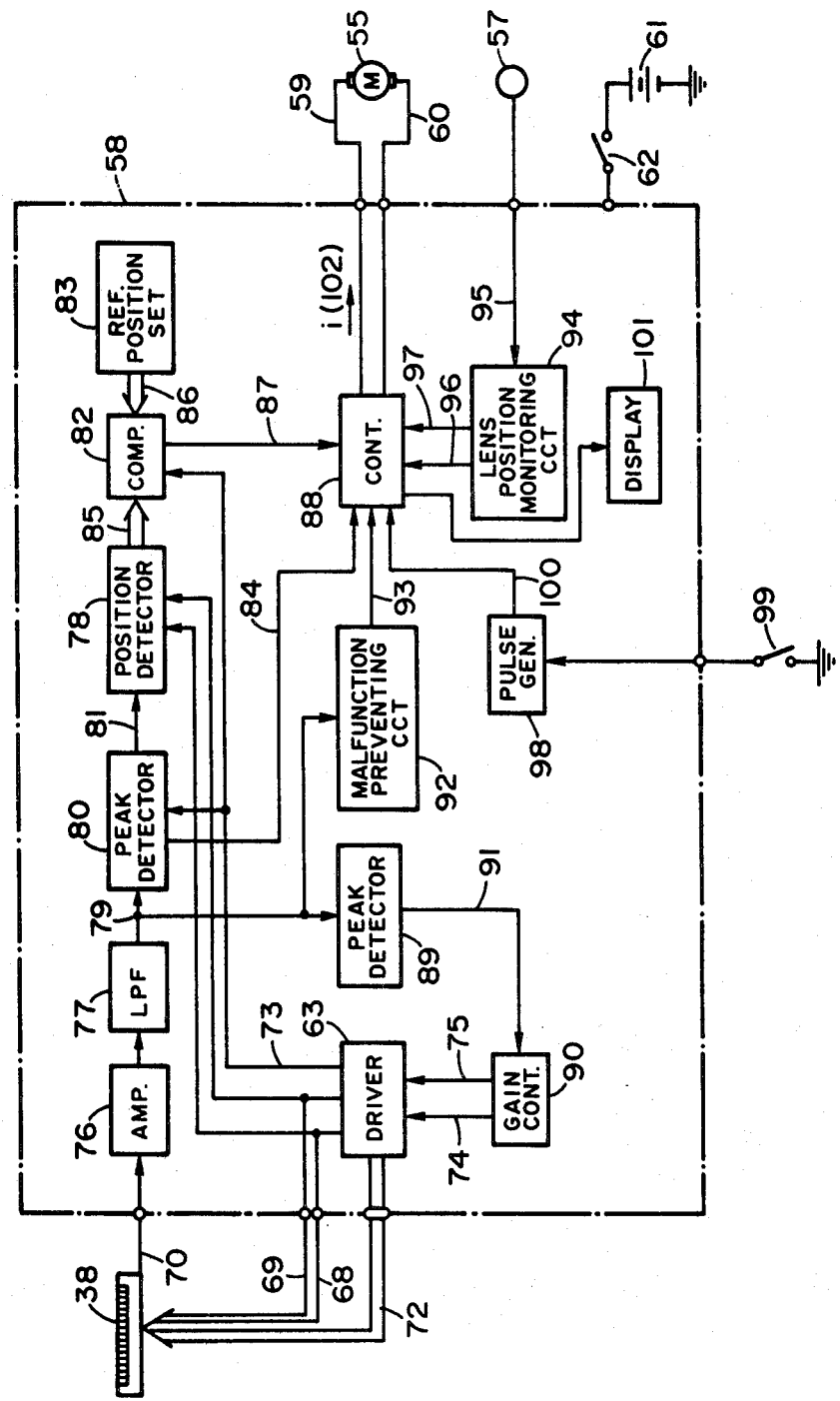
FIG. 9 is a block diagram of the electric system of the embodiment.

FIG. 9 is a block diagram of the signal processor 58. In FIG. 9, reference numeral 38 designates the same linear photo-sensor array as shown in FIG. 1. For a better understanding of the electrical system in the embodiment of the invention, we will make, at first, a further detailed description of the sensor array 38.

Figure 10:
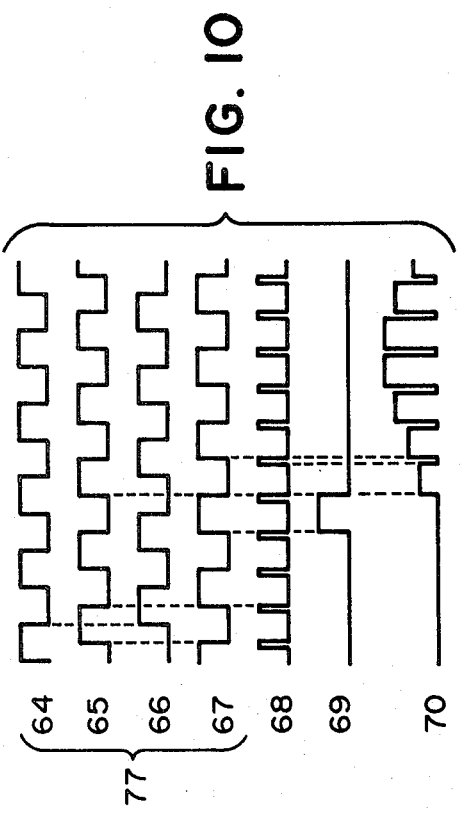
FIGS. 10 and 11 are wave form charts thereof.

The sensor array 38 receives photo signals and puts out the corresponding electric signals sequential in times series in accordance with output signals 68, 69 and 72 from a driver 63. The sensor array used in this embodiment operates in the manner shown in FIG. 10.

Figure 11:
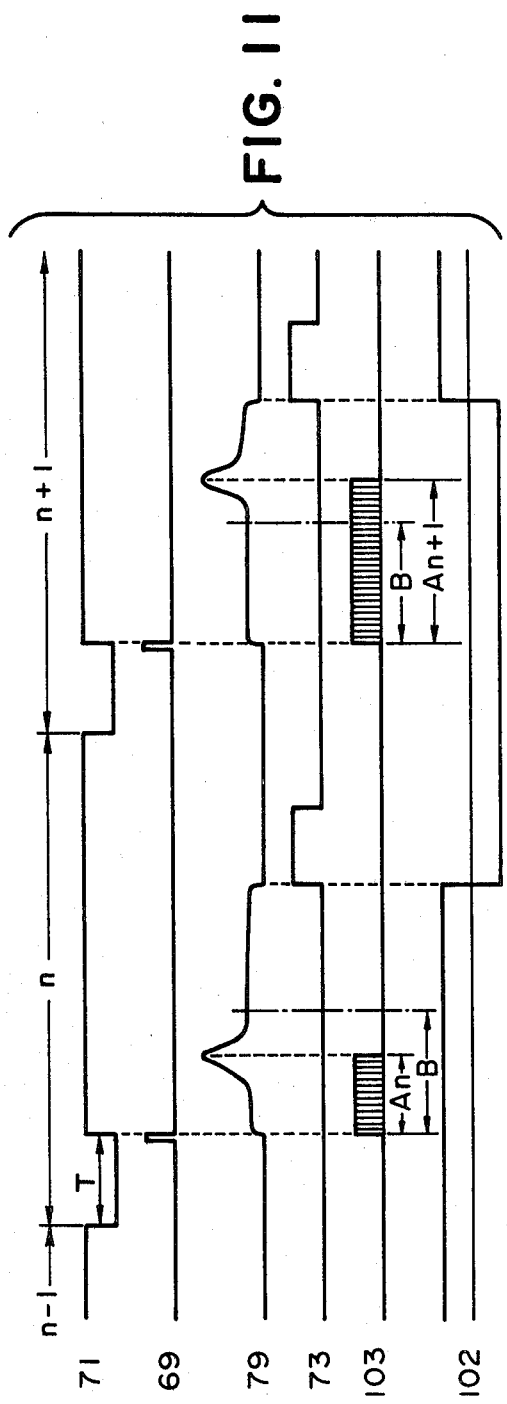

As shown in FIG. 11, photo inputs are stored in individual photo diodes of every bit during a low level pulse period T when the integration control gate (ICG) signal 71 is at low level. The stored electric charges are transferred to a shift register in accordance with the shift (SH) pulse 69. The transferred charges are sequentially put out as output 70 in accordance with clock signals $\phi_1$-$\phi_4$(64-67). The output stage of the sensor array is reset by the resetting (RS) pulse 68. The resetting pulse 68 serves to erase the charge in the previous bit prior to output from the next bit. In this embodiment, this RS pulse is used also as a bit synchronizing signal. Signal 72 contains only clocks 64-67 and ICG 71 of the sensor array driving signals while excluding RS pulse 68 and SH pulse 69 therefrom.

Now referring to FIG. 9, the driver generates a pulse 73 in synchronism with the end of reading in addition to the above mentioned RS pulse 68, SH pulse 69 and signal 72. Further, the driver has a function to change the storing time T when it receives storing time (T) changing signals 74, 75. Designated by 76 is an amplifier, 77 is a low-pass filter (LPF) and 80 is a peak detector. LPF 77 serves to remove the fluctuation of signal 70 caused by RS pulse 68. The peak detector 80 detects the position of focus mark as a peak position of signal. When the signal contains no peak beyond a certain determined value, the peak detector generates a signal on the line 84 at a high level and issues, as signal 81, a pulse synchronized with the pulse 73. Reference numeral 78 designates a position detector, 82 is a comparator and 83 is a reference position setting circuit.

As seen best in FIG. 11, at waveform 103, the position detector 78 starts counting RS pulses 69 in response to SH pulse and stops counting in response to pulse 81. The result of counting A is introduced into the comparator 82 as output 85 in FIG. 9. The comparator receives also the signal of reference position B (output 86) preset by the reference position setting circuit 83 A (output 85) and B (output 86) are compared in the comparator 82 and the result of comparison is introduced into a controller 88.

89 is a peak detector for detecting the peak value 91 of the signal 79. Designated by 90 is a gain controller which receives the peak value 91 and puts out signals 74, 75 for controlling the storing time T. The signal 79 is introduced also into a malfunction preventing circuit 92. The malfunction preventing circuit makes the level of output 93 high when the signal 79 contains any error signal superposed thereon resulting, for example, from winking or vigetting.

94 is a lens position monitoring circuit which receives output 95 from the potentiometer 57 shown in FIG. 1 and monitors the position of the focusing lens 3. When the focusing lens 3 is located in a position beyond the predetermined range of measuring visibility (followable range) in the direction of (+) or (−), the monitoring circuit 94 makes the signal 96 or 97 high level respectively. 98 is a pulse generator for generating pulse 100. Switch 99 is closed in synchronism with the shutter 7 (FIG. 1.). The pulse 100 is generated in synchronism with turning on of the switch 99 and the level of the pulse becomes high during the shutter opening time (exposure time). During the high level period of pulse 100, the motor 55 is maintained in stopped condition. The controller 88 receives signals 84, 87, 93, 96, 97 and 100 to control the rotation of the motor 55. When the signal 93 is at high level, that is, when any error signal is present, the motor 55 is stopped and remains stopped until the level of signal 93 is turned to low level. If the signal 84 is at high level, namely if no focus position is detected, then the controller 88 makes the motor 55 rotate repeatedly in response to the aforementioned range signal 96 or 97 so that the focusing lens 3 is moved reciprocatively within the followable range. This reciprocating movement of the focusing lens is repeated many times until the focus mark position is detected. However, if the number of reciprocations is over a certain predetermined value, the motor is stopped and instead a display circuit 101 gives the examiner an alarm which may be an acoustic signal or a visual signal or a combination thereof. This warning display can be reset by opening the switch 62.

In the above, the manner of operation of the illustrated embodiment has been described in connection with abnormal operation wherein either signal 84 or signal 93 is at high level. In case that both of signals 84 and 93 are at low level (normal operation), the apparatus operates in the manner shown in FIG. 11. As an example, FIG. 11 shows such case wherein A<B at the n-th scanning and A>B at the n+1th scanning. When A>B, current i (102) is made to flow into the motor in the direction indicated by the arrow in FIG. 9.

The result of comparison 87, for instance, at the n-th scanning is put out in synchronism with the rising of pulse 73 and the direction of flow of the current i (102) is reversed. The motor continues to rotate until the output of SR pulse at the next scanning. However, when A=B, the current i (102) becomes zero and therefore the motor 55 is stopped. Also, in the case where the visibility of the eye to be examined is out of the followable range in the state of normal operation of the apparatus, either of the range signals 96 and 97 become high and therefore the motor 55 is stopped. The display circuit 101 generates an acoustic or visual warning signal in the same manner as in the aforementioned case. The warning display can be reset by opening the switch 62.

The circuit 58 described above is powered by closing the switch 62 to start scanning of the photo-sensor array 38. The output signal from the sensor array 38 is delivered to the amplifier 76 and then to LPF 77 to form the signal 79. The signal 79 is put into the peak detector 80 which detects the height of the peak of the signal. The gain control circuit 90 is brought into operation and changes the storing time T in accordance with the detected height of the signal peak. Thus, a certain value of storing time is selected which is most suitable for obtaining a proper signal level. In this state, outputs 70 from the sensor array 38 are sequentially read out and subjected to a determined electrical processing. The position detector 78 detects the bit at which the focus mark is formed. The comparator 82 compares the detected position A with the reference position B. In the manner described above, the motor 55 is rotated through the controller 88 in a direction to attain A=B. When the focusing lens 3 and the focus mark projection system 25 are adjusted to the position in which A=B, the motor 55 is stopped. Thus, focusing of the fundus camera is completed. However, even when the subject person is gazing at a fixation mark, the refractive power of his eye may vary minutely and also his head may move forward and backward to some extent. This results in fluctuation of the in-focus state. To compensate for such out-of-focus condition, the motor 55 is operated to follow the fluctuation of focus.

When the shutter 7 is released by the examiner, the switch 99 is closed and the pulse 100 is issued from the generator 98. The motor 55 is stopped independently of signal 87 to prevent the focusing lens 3 from being moved during taking of a picture. At the end of exposure, the level of pulse 100 becomes high and focus adjustment is again executed depending upon the signal 87 for taking of the next picture.

While the invention has been particularly shown and described with reference to preferred embodiments thereof, it will be understood by those skilled in the art that the foregoing and other changes in form and details can be made therein without departing from the spirit and scope of the invention.

What we claim is:

1. An eye-fundus camera comprising:
    means for obtaining a picture of the fundus of an eye being examined and including illumination means for illuminating the fundus with an illumination light of wavelength within a first range, imaging optical means for forming an image of the illuminated fundus, photodetecting means for detecting the image, and focusing means for causing said optical means to focus the image on said detecting means;
    mark forming means for forming a detection mark on the fundus with light of wavelength within the first range and light of wavelength within a second range different from the first range, operation of said mark forming means being coordinated with said focusing means;
    photosensing means disposed in an optical path of said imaging optical means for sensing the detection mark reflected from the fundus;
    filtering means for filtering the light incident on said photosensing means, said filtering means being able to cut off said light of wavelength within the first range and to transmit light of wavelength within the second range;
    observation means disposed in an optical path of said imaging optical means for permitting an observer to observe the fundus and the detection mark and also for providing a visual field for observation by the observer;

comparative mark providing means for providing a comparative mark locatable in the visual field for observation relative to the detection mark reflected from the fundus in a predetermined relation when said focusing means causes said optical means to focus the image on said photo-detecting means; and control means for operating said focusing means and said mark forming means until the detection mark and the comparative mark are located in the predetermined relation, whereby said focusing means causes said optical means to focus the image on said photo-detecting means.

2. An eye-fundus camera as set forth in claim 1 wherein said first wavelength range is the range of visible light.

3. An eye-fundus camera as set forth in claim 1 wherein said second wavelength range is the range of infrared light.

4. An eye-fundus camera as set forth in claim 1 wherein said filtering means is a wavelength selecting mirror disposed between said imaging optical means and said photo-detecting means.

5. An eye-fundus camera as set forth in claim 1 wherein said comparative mark providing means further forms a detection mark on said fundus with light of wavelength within the first range and cooperates with said focusing means.

6. An eye-fundus camera as set forth in claim 1, which further comprises a barrier filter which is removably interposed in said imaging optical means and which transmits light of wavelength within the second range.

7. An eye-fundus camera comprising:

illumination means for illuminating the fundus of an eye being examined with light in the visible range;

means for obtaining a picture of the illuminated fundus and including, in optical order, an objective lens, aperture means, a relay lens, means for selecting an optical path and photographic film said obtaining means being operable to focus an image of the fundus on said photographic film;

viewing means optically connected with said selecting means and disposed for viewing said fundus;

projection means for projecting on the fundus a first detecting light containing visible rays and infrared rays and a second detecting light containing visible rays;

a wavelength selecting mirror disposed between said relay lens and said photographic film for transmitting visible rays but reflecting infrared rays;

a linear photosensor array for sensing the position of the first detecting light, as reflected from said fundus and then reflected by said wavelength selecting mirror, relative to a reference position indicating that the image of the fundus is focused on said photographic film, and for producing an output indicative of said sensing; and focus controlling means for operating said obtaining means and projection means to cause said obtaining means to focus the image of the fundus based on one of the output from said linear photosensor array and manual operation of said obtaining means.

8. An eye-fundus camera as set forth in claim 7 which further comprises a barrier filter which is removably interposed between said aperture means and said wavelength selecting mirror and which transmits infrared rays.

9. An eye-fundus inspection apparatus comprising:

a camera having illuminating means for illuminating the fundus of an eye being examined, objective optical means positionable in opposition to the eye being examined, imaging optical means for receiving light from said objective optical means and forming an image of the fundus, image receiving means for detecting the image formed by said imaging optical means, and focusing means for focusing the camera on the fundus of the eye;

focus mark projecting means for projecting, on the fundus through said objective optical means, at least two focus marks one of which is formed by light of wavelength in a first range and the other of which is formed by light of wavelength within at least a portion of the first range and light of wavelength within a range different from the first range, said focus mark projecting means being operationally associated with said camera for placing said focus marks in a predetermined positional relation with each other when said focus marks are focused on the fundus and said camera is focused on the fundus and for placing said focus marks out of said predetermined positional relation when said marks are defocused on the fundus and said camera is defocused on the fundus;

focus mark detecting means for detecting the positional relation of said focus marks reflected from the fundus and emerging from said objective optical means, said focus mark detecting means having photosensing means for detecting one of said focus marks, and wavelength selecting means for permitting incidence on said photosensing means, only of light of wavelength within the second range, said photosensing means operating said focusing means and said focus mark projecting means until said focus marks are put in said predetermined positional relation; and viewing means optically coupled with said camera and for viewing the fundus and said focus marks.

10. An eye fundus inspection apparatus according to claim 9, wherein said second wavelength range is the range of infrared light.

11. An eye-fundus inspection apparatus according to claim 9, wherein said wavelength selecting means comprises a dichroic mirror.

12. An eye-fundus inspection apparatus according to claim 9, further comprising a barrier filter disposed between said objective optical means and said image receiving means, said barrier filter transmitting therethrough light of wavelength within said second wavelength range for fluorescent photography.

* * * * *

UNITED STATES PATENT AND TRADEMARK OFFICE
CERTIFICATE OF CORRECTION

PATENT NO. : 4,436,388
DATED : March 13, 1984
INVENTOR(S) : JUNICHI TAKAHASHI ET AL.

It is certified that error appears in the above-identified patent and that said Letters Patent is hereby corrected as shown below:

IN THE ABSTRACT

Line 12, between "is" and "with" insert --formed--.

Column 1

Line 12, change "alreaady" to --already--;

Line 13, change "application" to --Application--;

Line 15, change "application" to --Application--;

Line 17, change "Arts" to --Art--;

Line 26, change "patent application" to --Patent Application--;

Line 45, change "quantity" to --quality--;

Line 53, between "deflect" and "reflected" insert --a--;

Line 55, change "being" to --is--.

Column 2

Line 46, change "dichoric" to --dichroic--.

UNITED STATES PATENT AND TRADEMARK OFFICE
CERTIFICATE OF CORRECTION

PATENT NO. : 4,436,388

DATED : March 13, 1984

INVENTOR(S) : JUNICHI TAKAHASHI ET AL.

It is certified that error appears in the above-identified patent and that said Letters Patent is hereby corrected as shown below:

Column 3

Line 22, change "20" to --21--.

Column 7

Line 45, change "is called also" to --is also called a--;

Line 64, change "photosensor" to --photo-sensor--.

Column 8

Line 9, change "exciter" to --excitor--;

Line 14, change "exciter" to --excitor--;

line 65, change "83 A" to --83. A--.

Column 9

Line 16, change "high level respectively" to --a high-level signal--;

Line 33, change "reciprocatively" to --reciprocally--;

Line 45, delete "that", and delete "of";

UNITED STATES PATENT AND TRADEMARK OFFICE
CERTIFICATE OF CORRECTION

PATENT NO. : 4,436,388

DATED : March 13, 1984

INVENTOR(S) : JUNICHI TAKAHASHI ET AL.

It is certified that error appears in the above-identified patent and that said Letters Patent is hereby corrected as shown below:

Line 61, change "either of the range signals 96 and 97 become" to --either range signal 96 or 97 becomes--.

Signed and Sealed this

Thirtieth Day of October 1984

[SEAL]

Attest:

GERALD J. MOSSINGHOFF

Attesting Officer

Commissioner of Patents and Trademarks